United States Patent [19]

Towersey et al.

[11] Patent Number: 4,466,988

[45] Date of Patent: * Aug. 21, 1984

[54] EDIBLE PROTEIN CONTAINING SUBSTANCES

[75] Inventors: Peter J. Towersey, Wycombe; John Longton, Berkhamsted; Geoffrey N. Cockram, Exeter, all of England

[73] Assignee: Ranks Hovis McDougall Limited, London, England

[*] Notice: The portion of the term of this patent subsequent to Mar. 9, 1994 has been disclaimed.

[21] Appl. No.: 809,018

[22] Filed: Jun. 22, 1977

Related U.S. Application Data

[63] Continuation-in-part of Ser. No. 584,451, Jun. 6, 1975, abandoned, and Ser. No. 507,123, Sep. 18, 1974, Pat. No. 4,041,189, said Ser. No. 584,451, is a continuation of Ser. No. 440,775, Feb. 8, 1974, Pat. No. 3,937,693.

[30] Foreign Application Priority Data

Sep. 24, 1973 [GB] United Kingdom ............... 44708/73
Oct. 8, 1975 [GB] United Kingdom ................ 7087/75

[51] Int. Cl.$^3$ ............................................. A23J 1/18

[52] U.S. Cl. ............................... 426/656; 260/112 R

[58] Field of Search .................. 195/1, 2, 28 R, 28 N, 195/98, 104; 260/112 R; 426/62, 656

[56] References Cited

U.S. PATENT DOCUMENTS

| | | | |
|---|---|---|---|
| 3,139,385 | 6/1964 | Ogata et al. | 195/28 N |
| 3,243,354 | 3/1966 | Nakao et al. | 195/28 N |
| 3,634,194 | 1/1972 | Frankenfeld et al. | 195/28 N |
| 3,686,144 | 8/1972 | Tamura et al. | 426/656 X |
| 3,775,393 | 11/1973 | Akin et al. | 260/112 R |
| 3,809,776 | 5/1974 | Chao | 426/656 X |
| 4,061,781 | 12/1977 | Solomons et al. | |

*Primary Examiner*—Robert A. Yoncoskie
*Attorney, Agent, or Firm*—Stevens, Davis, Miller & Mosher

[57] ABSTRACT

A fermentation product comprising a nonviable edible proteinaceous mass derived from a non-toxic fungal mycelium of a non-toxic strain of Fusarium preferably selected from the group consisting of *Fusarium graminearum*, *Fusarium solani* and *Fusarium oxysporum* possessing a reduced level of RNA of below 4%.

6 Claims, No Drawings

EDIBLE PROTEIN CONTAINING SUBSTANCES

This application is a continuation-in-part of application Ser. No. 584,451 filed June 6, 1975, now abandoned, and application Ser. No. 507,123 filed Sept. 18, 1974, now U.S. Pat. No. 4,041,189. Application Ser. No. 584,451 is a continuation of application Ser. No. 440,775 filed Feb. 8, 1974, now U.S. Pat. No. 3,937,693.

This invention is for improvements in or relating to the production of edible protein containing substances.

It has particular reference to a process for reducing the nucleic acid content of microfungi.

Our Specification No. 1,210,356 describes and claims a process for the production of an edible protein-containing substance which comprises incubating and proliferating, under aerobic conditions, an organism which is a non-toxic strain of a microfungus of the class Fungi Imperfecti, in a culture medium containing essential growth-promoting nutrient substances, of which carbon in the form of assimilable carbohydrate constitutes the limiting substrate in proliferation, and separating from the assimilable carbohydrate exhausted medium the proliferated organism which constitutes the edible protein-containing substance.

Our application No. 8977/70 (Ser. No. 1,331,471) describes and claims a process for the production of an edible protein-containing substance which comprises incubating and proliferating, under aerobic conditions, a non-toxic strain of *Penicillium notatum* or *Penicillium chyrsogenum* or a variant or mutant thereof, in a culture medium containing essential growth-promoting nutrient substances, of which carbon in the form of assimilable carbohydrate constitutes the limiting substrate in proliferation, and separating from the assimilable carbohydrate exhausted medium the proliferated organism which constitutes the edible protein-containing substance.

Our application No. 8978/70 (Ser. No. 1,331,472) describes and claims our specific novel strain of *Penicillium notatum-chrysogenum* IMI 138291 and variants and mutants thereof.

Our application No. 30584/70 and cognate No. 10466/71 (Ser. No. 1,346,062) describes and claims a process for the production of an edible protein-containing substance which comprises incubating and proliferating, under aerobic conditions, a non-toxic strain of the genus Fusarium or a variant or mutant thereof, in a culture medium containing essential growth-promoting nutrient substances, of which carbon in the form of assimilable carbohydrate constitutes the limiting substrate in proliferation, and separating the proliferated organism comprising the edible protein-containing substance. The corresponding U.S. Patent is U.S. Pat. No. 3,937,654.

Our British specification contains the following disclosure:

The present invention relates to a process for the production of edible protein-containing substances and has particular reference to the production of fungal protein by microbial action.

Our Specification No. 1210356 relates to a process for the production of an edible protein-containing substance which comprises incubating and proliferating, under aerobic conditions, an organism which is a non-toxic strain of a microfungus of the class Fungi Imperfecti, in a culture medium containing essential growth-promoting nutrient substances, of which carbon in the form of assimilable carbohydrate constitutes the limiting substrate in proliferation, and separating from an assimilable carbohydrate exhausted medium the proliferated organism which constitutes the edible protein-containing substance.

Our copending application No. 8977/70, Ser. No. 1,331,471, claims an edible protein-containing substance comprising fungal mycelium possessing a high net protein utilisation value on rat assays of at least 70 based on the α-amino nitrogen.

It is also an object of the present invention to provide an edible protein-containing substance comprising non-toxic fungal mycelium possessing a high net protein utilisation value on rat assays of at least 65 preferably at least 70 based on the α-amino nitrogen and containing a non-toxic strain of the genus Fusarium or a variant or mutant thereof. The non-toxic mycelium possessing a high net protein utilisation value of at least 70 based on the α-amino nitrogen may contain a non-toxic strain of the species *Fusarium graminearum*.

According to the present invention there is provided a process for the production of an edible protein-containing substance which comprises incubating and proliferating, under aerobic conditions, a non-toxic strain of the genus Fusarium or a variant or mutant thereof, in a culture medium containing essential growth-promoting nutrient substances, of which carbon in the form of assimilable carbohydrate constitutes the limiting substrate in proliferation, and separating the proliferated organism comprising the edible protein-containing substance.

The separated proliferated organism comprising the edible protein-containing substance may be incorporated into a foodstuff for human or animal consumption.

The substrate employed in the incubation stage may be of vegetable origin, for example starch, starch containing materials or products of their hydrolysis, sucrose, sucrose containing materials or hydrolysed sucrose i.e. invert sugar or mixtures thereof. Thus the substrate may comprise hydrolysed potato, molasses, glucose, maltose, hydrolysed bean starch or cassava. Alternatively substrate of animal origin comprising whey may be employed.

The non-toxic strain of Fusarium may be a strain of *Fusarium graminearum*.

The preferred non-toxic strain is our strain of *Fusarium graminearum* Schwabe, which is described and claimed together with variants and mutants thereof in copending United Kingdom application No. 23452/70 (Ser. No. 1346061), has been deposited at the Commonwealth Mycological Institute, Kew, and assigned the number IMI 145425. It is non-pathogenic to wheat.

Our copending United Kingdom application No. 23452/70 (Ser. No. 1346061) also describes and claims specifically five variants of our strain of *Fusarium graminearum* Schwabe IMI 145425 namely I-7, I-8, I-9, I-15 and I-16 deposited with the Commonwealth Mycological Institute and assigned the numbers IMI 154209, IMI 154211, IMI 154212, IMI 154213 and IMI 154210 respectively.

The temperature of incubation is in general between 25° and 34° C., preferably around 30° C.

Inoculation resulting in commencement of the process is carried out by a pregerminated seed stage comprising for example from 2% to 10% of inoculum, usually in the range 5% to 10% of inoculum based on final fermented operating volume.

The pH of the substrate medium during incubation is preferably kept within a suitable range supporting maximum growth, for example, between 3.5 to 7.

The period of growth in batch culture under the above-mentioned conditions is usually found to range from 20 to 48 hours. In both batch and continuous processes aeration and agitation should be carried out to provide a sufficient level of dissolved oxygen to overcome deficiency which can be a limiting growth factor.

As will be well understood by those skilled in the art sufficient quantities of essential growth nutrients such as nitrogen, sulphur, phosphorus and other trace elements are maintained in the substrate medium so that growth of the substrate is limited only by the carbohydrate available to the fungus.

In addition to the nutrients stated above the presence of one or more vitamins such for example as biotin may be desirable to maintain maximum growth rate.

It is also desirable to add a non-toxic anti-foaming agent to the substrate medium to control foaming during the fermentation.

The substance produced according to the present invention may be isolated in any suitable manner known in the art. Thus the resulting mycelium may be recovered by separation, washing, filtration and drying. In this connection, however, it has been found that if the moisture content of the substance is reduced below a critical level of about 50% (w/w) by filtration under pressure the subsequent drying methods employed are not subjected to such stringent temperature limitations which is an important factor in the economic processing of these materials. The method of drying must not cause damage to the nutritional value of the mycelium and may be drying in a current of air at 75° C. or freeze drying.

The fungal mycelium produced by the process of the present invention shows very good water binding capacity and may be useful as a thickening and gelling agent. Not being an isolate, it retains its vitamins as well as other nutritionally available materials such as lipids and some carbohydrates. Fungal mycelium has satisfactory baking characteristics which are of value in protein enriched breads, breakfast foods and food snacks. The fungal mycelium, because of its filamentous structure, can be baked, fried or puffed and presented to many communities as a food comparable in appearance and acceptability with conventional foods which they are accustomed to eating.

Following is a description by way of example of methods of carrying the invention into effect.

Culture medium or medium percentages given are as weight per unit volume (w/v) or volume per unit volume (v/v) for solids and liquids respectively Definitions:

NPU = net protein utilisation

NPUop = net protein utilisation: operative $\mu$: a specific growth rate which is the rate of increase/unit of organism concentration $$\left( \frac{1}{x} \frac{dx}{dt} \right).$$

$\mu_{max.}$ is the growth rate constant (the maximum value of $\mu$ at saturation levels of substrate).

Yield Factor: weight of organism formed/weight of substrate used.

Examples 1–4 are of batch culture.

EXAMPLE 1

10 Liters of the following culture medium were prepared and sterilised as described in a stirred fermenter vessel.

| Cane molasses to provide | 6% w/v sugar |
|---|---|
| Ammonium sulphate | 1.2% |
| NaH$_2$PO$_4$ | 0.25% |
| Sterilised 30 minutes | 15 psig |
| CaCO$_3$ | 0.5% w/v |
| Sterilised 3 hours | 15 psig |

The medium components were added aseptically and attemperated to 30° C. An inoculum equivalent to 5–10% by volume of the culture medium and grown either on a glucose/corn steep liquor medium or other suitable materials in shake flasks was inoculated with a spore suspension of the organism comprising our strain of *Fusarium graminearum* Schwabe IMI 145425, for 18–24 hours at 30° C. on a rotary shaker, and added aseptically to the fermenter.

The fermenter incubated at 30° C. was then stirred at 800 rpm with a 6 bladed disc turbine (0.5D) in a full baffled vessel and 1 VVM of sterile air passed through. After 35 hours, the grown mycelium was removed from the fermenter, centrifuged, washed with water and dried in a warm air band drier, air temperature 75° C.

The dried product had the following composition:

| | |
|---|---|
| Total Nitrogen | 8.0% |
| Ash | 5.3% |
| Lipid | 2.7% |
| NPUop. | 52 based on Total Nitrogen |

EXAMPLE 2

10 Liters of the following culture medium were prepared and sterilised as described, in a 14 liter New Brunswick, Microferm, fermenter.

| | | | Final % |
|---|---|---|---|
| Solution 1 | Glucose | pH 3.0 | 3.0 |
| Solution 2 | Ammonium sulphate | | 0.7 |
| Solution 3 | Potassium di-hydrogen phosphate | pH 5.0 | 1.0 |
| Solution 4 | $FeSO_47H_2O$ | pH 2.5 | 0.001 |
| | $MnSO_44H_2O$ | | 0.0005 |
| | $CuSO_45H_2O$ | | 0.0001 |
| | $MgSO_47H_2O$ | | 0.025 |
| Solution 5 | $Na_2MoO_42H_2O$ | | 0.0001 |
| | $CoCl_26H_2O$ | | 0.0001 |
| | $CaCl_22H_2O$ | | 0.0015 |
| Solution 6 | NaOH | | 0.1 |

All the above solutions were sterilised by heat for 15 minutes at 15 psig. Solution 7 Vitamins and/or amino acids as described below sterilised by filtration.

The solutions were added aseptically to the vessel.

An inoculum was grown and added as in Example 1 except that the final concentration in the fermenter was adjusted so as to provide 0.5 gm/l dry wt. of mycelium.

The conditions of growth were temperature 30° C.; aeration 1 VVM, stirrer speed was adjusted to maintain a level of dissolved oxygen above 25% of the saturation value in the culture medium, measured by a New Brunswick Inc. DO probe. Sterile anti-foam, polypropylene glycol 2000, was added as required to suppress foam and pH was maintained between 6.0–6.3 by the addition of sterile potassium hydroxide solution.

| | | Growth rates (hr.$^{-1}$) |
|---|---|---|
| (i) | Omitting solution 7 (Minimal medium) | very slow |
| (ii) | Solution 7 such that the final concentration of Biotin in the culture medium was 50 µg/l | 0.2 |
| (iii) | Solution 7 such that the final concentration of Biotin in the culture medium was 50 µg/l; Choline chloride 30 mg/l and Methionic 300 mg/l | 0.25 |

EXAMPLE 3

Medium and conditions were as in Example 2, but the glucose was replaced with maltose.

| | | |
|---|---|---|
| (i) | Solution 7 as Example 2 (ii) | 0.18 |
| (ii) | Solution 7 as Example 2 (iii) | 0.21 |

EXAMPLE 4

100 Liters of the following culture medium were prepared and sterilised as described in a 130 l stainless steel fermenter.

| | % final concentration |
|---|---|
| Glucose | 4.0 |
| Corn steep liquor (50% Total Solids) | 0.8 |
| Ammonium sulphate | 0.2 |
| Potassium di-hydrogen phosphate | 0.2 |
| $MgSO_4 \cdot 7H_2O$ | 0.025 |
| $ZnSO_4 \cdot 7H_2O$ | 0.0005 |
| $FeSO_4 \cdot 7H_2O$ | 0.0005 |
| $MnSO_4 \cdot 4H_2O$ | 0.0001 |

The medium was sterilised at pH 3.0 at 15 psig for 30 minutes and on cooling to 30° C. adjusted to pH 5.0 by the sterile addition of ammonia.

Biotin sterilised by filtration to give 40 µg/l final concentration, was added aseptically.

The vessel was inoculated with 10 liters of culture grown in a sparged vessel, for 18 hours, at 30° C., on a medium containing: Glucose 2%; tryptone ("Oxoid") 0.4%; yeast extract ("Oxoid") 0.1%; ammonium sulphate 0.15%; potassium di-hydrogen phosphate 1%; sodium hydroxide 0.1%; magnesium sulphate 0.025%; ferrous sulphate 0.001%; zinc sulphate 0.001%; manganese sulphate 0.0005%; copper sulphate 0.001%; anti-foam, polypropylene glycol 2000 0.05% and sterilised for 45 minutes at 15 psig, inoculated with a spore suspension of our organism *Fusarium graminearum* Schwabe IMI 145425. The word "Oxoid" is a Registered Trade Mark.

The conditions for growth were temperature 30° C., aeration adjusted to provide dissolved oxygen concentrations above 10% of the saturation value for the culture broth. Sterile anti-foam, polypropylene glycol 2000, was added to suppress foaming, and the pH was maintained at 5.0 by means of sterile ammonia additions. Samples of the mycelium were taken at intervals over the period of batch culture, filtered, washed with water and dried. On dry weight basis analysis gave Total nitrogen 8.0–8.6%; α-Amino nitrogen 6.4–6.6%. The initial growth rate in this complex medium derived from both the batched culture medium and inoculum was approximately 0.3 hr.$^{-1}$.

The following examples 5 and 6 are of continuous culture.

EXAMPLE 5

Culture medium of the following composition was prepared:

| | Final % |
|---|---|
| Solution 1 | |
| Glucose | 3.0 |
| Ammonium sulphate | 0.25 |
| Potassium di-hydrogen phosphate | 0.3 |
| Magnesium sulphate | 0.025 |
| Anti-foam, polypropylene glycol 2000 | 0.01 |
| Sterilised at pH 3.0 for 30 minutes at 15 psig | |
| Solution 2 | |
| $MnSO_4 4H_2O$ | 0.0005 |
| $FeSO_4 7H_2O$ | 0.0005 |
| $ZnSO_4 7H_2O$ | 0.0005 |
| $CoCl_2 6H_2O$ | 0.0001 |
| $CuSO_4 5H_2O$ | 0.0001 |
| $NaMoO_4 2H_2O$ | 0.0001 |
| Sterilised 15 minutes at 15 psig | |
| Solution 3 | |
| Vitamins and or amino acid as described below sterilised by filtration. | |

All solutions were added as necessary, aseptically. In 8.5 liter chemostat the conditions of growth were as follows:

Temperature 30° C.; aeration 1 VVM; agitation 800 rpm single 6 bladed disc turbine 0.5 D in fully baffled vessel. Organism, our strain of *Fusarium graminearum* Schwabe IMI 145425. The pH maintained at 5.0 by automatic addition of sterile ammonia.

Samples were taken, filtered, washed with water and dried.

| | | μ Max. hr.$^{-1}$ | Yield factor | Mycelium TN % | Mycelium AN % | NPU based on TN | NPU based on AN |
|---|---|---|---|---|---|---|---|
| (i) | Solution 3 such that the final concentrate of Biotin in the culture medium was 20 μg/l | 0.17–0.19 | 0.5 | 7.2 to 7.9 | 6.3 to 6.8 | 54 | 65 |
| (ii) | Solution 3, such that the final concentration of Biotin in the culture medium was 20 μg/l and of methionine was 600 mg/l | 0.20–0.21 | 0.5 | 7.7 to 8.6 | 6.1 to 6.5 | 59 | 78 |

EXAMPLE 6

Culture medium of the following composition was prepared:

|  | % |
|---|---|
| Bean starch (α-amylase treated) | 3.0 carbohydrate |
| Corn steep liquor | 1.33 |
| Ammonium sulphate | 0.25 |
| Potassium di-hydrogen phosphate | 0.15 |
| Magnesium sulphate | 0.025 |
| Antifoam polypropylene glycol 2000 (v/w) | 0.025 |
| Sterilised pH 4.0 for 30 minutes at 15 p.s.i.g. | |

The medium was fed to the 8.5 liter chemostat under the same conditions as in Example 5 except that the pH was varied between 3.5 and 6.0 and growth rate throughout 0.1 hr$^{-1}$. Samples were taken, filtered, washed with water and dried. The following result was obtained:

|  | TN % | AN % | NPU based on TN | NPU based on AN |
|---|---|---|---|---|
| Product grown at pH 4.0 | 7.8 | 6.6 | 54 | 67 |
| Product grown at pH 5.0 | 8.6 | 7.1 | 57 | 71 |
| Product grown at pH 6.0 | 7.7 | 5.9 | 61 | 80 |

EXAMPLE 6(b)

The culture medium and conditions were as in Example 6 except that the pH was held at 5.0 throughout the run and the temperature was varied between 26° and 34° C. The optimum temperature was found to be 30°–32° C.

Examples 7 to 11 describe the fermentation of five variants or isolates of *Fusarium graminearum* Schwabe IMI 145425.

EXAMPLE 7

Duplicate shake flasks of 1-liter capacity were prepared containing 200 mls. of the following medium:

| | | Final concentration % |
|---|---|---|
| Solution 1 | Glucose (sterilised separately pH 3.0, 10 p.s.i./10 min.) | 3.0 |
| Solution 2 | Ammonium sulphate | 0.565 |
| | Potassium Dihydrogen Phosphate | 1.0 |
| | $MgSO_4{:}7H_2O$ | 0.025 |
| | $FeSO_4{:}(NH_2)_2SO_4{:}6H_2O$ | 0.0005 |
| | $MnSO_4{:}4H_2O$ | 0.0005 |
| | $CuSO_4{:}5H_2O$ | 0.0001 |
| | $CoCl_2{:}6H_2O$ | 0.0001 |
| | $CaCl_2{:}2H_2O$ | 0.0015 |
| | $Na_2MoO_42H_2O$ | 0.00001 |
| | NaOH | 0.2 |
| | Salts sterilised at 15 p.s.i.g./15 min. Final pH 6.0 | |
| Solution 3 | Vitamins as described below were sterilised by filtration | |

The solutions were added aseptically to give a final volume of 200 ml. then the flasks were inoculated with washed spores of our strain of *Fusarium graminearum* I-7 IMI 154209 to give a concentration of $8\times10^3$/ml.

The conditions of growth were temperature 30° C., 140 r.p.m. on orbital shaker with 2" throw.

At hourly intervals the growth was measured by measuring the Optical Density of a sample at 600 mμ. From the results obtained the following growth rates were established.

| | Growth rate $h^{-1}$ |
|---|---|
| (i) Solution 3 omitted (minimal medium) | very slow |
| (ii) Solution 3 such that the final concentration of Biotin in the culture medium was 50μg/l | 0.22 |
| (iii) Solution 3 such that the final concentration of Biotin in the culture medium was 50μg/l and Choline chloride 50 mg/l. | 0.27 |

EXAMPLE 8

The procedure of Example 7 was repeated but the strain I-7 was replaced by our strain of *Fusarium graminearum Schwabe I*-8. The following growth rates were established

| | Growth rate $h^{-1}$ |
|---|---|
| (i) As 7 (i) | very slow |
| (ii) As 7 (ii) | 0.22 |
| (iii) As 7 (iii) | 0.27 |

EXAMPLE 9

The procedure of Example 7 was repeated but the strain I-7 was replaced by our strain of *Fusarium graminearum* Schwabe I-9. The following growth rates were established:

| | Growth rate $h^{-1}$ |
|---|---|
| (i) As 7 (i) | very slow |
| (ii) As 7 (ii) | 0.21 |
| (iii) As 7 (iii) | 0.27 |

EXAMPLE 10

The procedure of Example 7 was repeated but the strain I-7 was replaced by our strain of *Fusarium graminearum* Schwabe I-15. The following growth rates were established:

| | Growth rate $h^{-1}$ |
|---|---|
| (i) As 7 (i) | very slow |
| (ii) As 7 (ii) | 0.21 |
| (iii) As 7 (iii) | 0.27 |

EXAMPLE 11

The procedure of Example 7 was repeated but the strain I-7 was replaced by our strain of *Fusarium graminearum* Schwabe I-16. The following growth rates were established:

| | Growth rate $h^{-1}$ |
|---|---|
| (i) As 7 (i) | very slow |
| (ii) As 7 (ii) | 0.21 |
| (iii) As 7 (iii) | 0.27 |

EXAMPLE 12

The procedure of Example 7 was repeated but the strain I-7 was replaced by the parent strain *Fusarium graminearum* Schwabe IMI 145425. The following growth rates were established:

|  | Growth rate $h^{-1}$ |
|---|---|
| (i) As 7 (i) | very slow |
| (ii) As 7 (ii) | 0.22 |
| (iii) As 7 (iii) | 0.27 |

Examples 13 and 14 describe fermentation using strains of Fusaria other than *Fusarium graminearum*.

EXAMPLE 13

A spore suspension of *Fusarium solani* strain A7-16 (IMI 154217) was inoculated into a seed fermenter of 80 liter volume containing a glucose, corn steep liquor medium. After growing up the seed fermenter to 10-20 gms per liter, it was split in two, 40 liters to each 400 liter vessel. The seed was inoculated into a medium of the following composition:

| | % |
|---|---|
| Starch | 6.0 |
| $KH_2PO_4$ | 0.20 |
| $(NH_4)_2SO_4$ | 0.25 |
| Corn Steep Liquor (50% Total Solids) | 0.50 | pH was 5.5 maintained by addition of sterile ammonia; Temperature 30° C. Pressure 30 p.s.i.g. Air rate 1.0 v.v.m. The revolutions of the stirrer were increased steadily from 92 to 184 r.p.m. to maintain dissolved oxygen in the vessel. The agitator consisted of two turbines 0.4D. When the carbohydrate had been utilised the grown mycelium was removed from the fermenter, filtered, washed with water, centrifuged, and dried in a warm air band drier at 75° C. The dried product had the following composition:

| | |
|---|---|
| Total nitrogen | 9.1% |
| Ash | 8.3% |

When fed to rats this material gave an NPUop of 41 based on Total Nitrogen.

EXAMPLE 14

*Fusarium oxysporum* strain A9-23 (IMI 154214) was grown exactly as in the previous example except the starch was replaced by cane molasses at a concentration that produced 6.0% sugars.

The dried product had the following composition:

| | |
|---|---|
| Total Nitrogen | 9.9% |
| Ash | 10.8% |
| NPUop | 47.0 based on Total Nitrogen |

Methods of analysis for Total Nitrogen (TN) Automatic Kjeldahl digestor (Technicon). A Ferrari, Ann. N.Y. Sci. 87, 792 (1960).

Amino nitrogen (AN) 2:4:6-Tri-nitro benzene sulphuric acid (modified). M. A. Pinnegar, Technicon Symposium 1965, p. 80.

Our Application No. 23452/70 (Ser. No. 1,346,061) describes and claims our specific novel strain of *Fusarium graminearum* Schwabe IMI 145425 and variants and mutants thereof.

The separated proliferated organism comprising the edible protein-containing substance obtained by the fermentation processes of our Applications Nos. 8977/70 (Ser. No. 1,331,471) and 30584/70 and Cognate No. 10466/71 (Ser. No. 1,346,062) may be incorporated into a foodstuff for human or animal consumption.

The processes of our Applications Nos. 8977/70 (Ser. No. 1,331,471) and 30584/70 and Cognate No. 10466/71 (Ser. No. 1,346,062) are capable of producing an edible protein-containing substance comprising fungal mycelium which possesses a high net protein utilisation value on rat assays of at least 70 based on the α-amino nitrogen.

If single-cell protein is to be used as a primary protein source for human consumption the Protein Advisory Group of the Food and Agricultural Organization (FAO) World Health Organisation (who) has advised that the nucleic acid content should be reduced to a level which would allow a maximum intake in the range of 2 grams of nucleic acid per day.

For a processing method to be acceptable, it must not only decrease the nucleic acid level to the required degree, but it also must be inexpensive and must not contaminate the food product with undesirable chemicals.

It is an object of the present invention to provide a process for the reduction of levels of nucleic acid in particular ribonucleic acid (RNA) in proliferated microorganisms combined with the minimum loss of protein to render them more acceptable as human food.

We have developed a process for treating cells of grown non-toxic microfungus of the class Fungi Imperfecti which can meet the above requirements of the World Health Organisation.

The invention provides fungal mycelium possessing a reduced level of RNA of below 4%.

Thus the invention provides fungal mycelium containing *Fusarium graminearum* Schwabe IMI 145425 possessing a reduced level of RNA of below 3% by weight, preferably below 2% by weight.

The invention also provides fungal mycelium containing *Penicillium notatum-chrysogenum* IMI 138291 possessing a reduced level of RNA of below 4%.

According to the present invention there is provided a process for reducing the nucleic acid content in the production of an edible protein-containing substance comprising contacting a grown non-toxic microfungus of the class Fungi Imperfecti with a solvent comprising between 40% and 100% (by volume) of a lower alkanol containing up to three carbon atoms and thereafter incubating at a pH between 5 and 9.5 and at a temperature between 30° C. and 80° C. for a time of at least 90 seconds.

The process may be applied to a grown non-toxic strain of Fusarium, *Penicillium notatum* or *Penicillium chrysogenum, Penicillium funiculosum* or *Aspergillus niger.*

The strain of Fusarium may be a strain of *Fusarium graminearum* Schwabe in particular IMI 145425, *Fusarium oxysporum* or *Fusarium solani* as described and claimed in our Applications Nos. 23452/70 (Ser. No. 1,346,061) and 30584/70 and Cognate No. 10466/71 (Ser. No. 1,346,062).

The strain of *Penicillium notatum* or *Pencillium chrysogenum* may be a strain of *Penicillium notatum-chrysogenum*, for example IMI 138291, as described and claimed in our Applications Nos. 8977/70 (Ser. No. 1,331,471) and 8978/70 (Ser. No. 1,331,472).

The lower alkanol containing up to three carbon atoms may be methyl alcohol, ethyl alcohol, propyl alcohol or isopropyl alcohol. Ethyl alcohol and isopropyl alcohol are solvents permitted by the Solvents in Food Regulations, 1967. The preferred solvent in the process of the present invention is isopropyl alcohol (IPA). Instead of pure isopropyl alcohol aqueous solutions containing between 40 or 50% by volume and up to 100% I.P.A. may be employed.

The incubation may conveniently be carried out at a temperature between 45° C. and 60° C. for a time of between 1.5 minutes and 40 minutes.

The incubation step may conveniently be carried out in the presence of a buffer solution for example $NH_4Cl/NH_4OH$ or $NH_4Cl/HCl$.

The post fermentation process of the present invention for reducing the nucleic acid content of microorganisms is essentially a two stage process.

Stage 1

The grown microbial protein or fungal mycelium obtained for example by the fermentation process described and claimed in our Applications Nos. 8977/70 (Ser. No. 1,331,471) and 30584/70 and Cognate No. 10466/71 (Ser. No. 1,346,062) may be harvested, filtered to remove growth medium and washed, if desired. It may then be suspended in the alkanol solvent for example for 1 minute at 20° C. or contacted with an alkanol solvent water mixture. The majority or all of the alkanol solvent may be removed by such methods as vacuum filtration, filter pressing or centrifugation. The duration of contact with the alkanol solvent may be varied but is generally in the range between 15 seconds and 15 minutes. The temperature may vary between 0° C. and 60° C.

Stage 2

The cells may then be brought into intimate contact with aqueous buffer solutions in the pH range 5 to 9.5. Thus the solvent treated cells may then be resuspended and incubated in aqueous buffer solution at pH 8.6 and temperature 45° C. An example of a suitable buffer solution is 0.1M ammonium chloride solution with ammonium hydroxide added to adjust the pH to 8.6.

The resulting treated cells may then be harvested again for example by filtration and washing with water and thereafter formulated into foods or dried by various methods.

When the process is carried out in the pilotplant the pH is adjusted to 5 after RNA removal. The purpose of this acidification is twofold (a) the material becomes "whiter" and (b) the texture changes and this enables harvesting by vacuum filtration to be carried out easier.

The resulting solvent treated microbial protein or fungal mycelium may have a RNA content of 1–4% compared to 7 to 10% of the untreated proliferated organism.

The cells may be analysed to determine their chemical composition and to evaluate the efficiency of the nucleic acid reduction process.

Following is a description by way of example of methods of carrying the invention into effect.

References to "Biomass Loss" denote weight lost during processing.

Ribonucleic acid (RNA) content was determined by a modification of the method of Schmidt G. and Thannhauser, S. J., J. Biol.Chem., 1945, 161, 83.

Method of analysis for Total Nitrogen (TN) Automatic Kjeldahl digestor (Technicon). A Ferrari, Ann. N.Y. Sci. 87, 792 (1960).

Amino nitrogen (AN) TNBS (modified). M. A. Pinnegar, Technicon Symposium 1965, p.80.

EXAMPLE A

Reduction of the Nucleic Acid Levels in Various Micro-Organisms

*Fusarium graminearum* IMI 145425 was cultivated by the following procedure:

Medium in distilled water:

| | |
|---|---|
| $K_2HPO_4$ | 15.05 $gL^{-1}$ |
| $(NH_4)_2HPO_4$ | 6.64 $gL^{-1}$ |
| tri Sodium Citrate | 15.7 $gL^{-1}$ |
| Citric Acid | 5.48 $gL^{-1}$ |
| $K_2SO_4$ | 1.0 $gL^{-1}$ |
| Choline chloride | 50 $mgL^{-1}$ |
| Biotin | 50 $\mu gL^{-1}$ |
| Glucose | 30 $gL^{-1}$ |

Minimal Salts

| | |
|---|---|
| $MgCl_2.6H_2O$ | 0.2 $gL^{-1}$ |
| $ZnSO_4$ | 0.003 $gL^{-1}$ |
| $MnCl_2 4H_2O$ | 0.005 $gL^{-1}$ |
| $FeCl_3.6H_2O$ | 0.01 $gL^{-1}$ |
| $CuCl_2.6H_2O$ | 0.001 $gL^{-1}$ |
| $NaMoO_4.2H_2O$ | 0.001 $gL^{-1}$ |
| $CoCl_2.6H_2O$ | 0.001 $gL^{-1}$ |
| $CaCl_2.2H_2O$ | 0.015 $gL^{-1}$ |

Sterilisation

All components with the exception of glucose are sterilised together, and the amounts of these materials required for 1 liter of medium are dissolved, made up to 850 ml. and distributed into 5 1 liter conical flasks, each containing 170 ml. A 30% w/v solution of glucose is prepared and sterilised in 20 ml. portions in universal bottles. Sterilisation is effected in an autoclave at 15 p.s.i. for 15 minutes.

Growth conditions

Before inoculation with 10 ml. of a growing culture, the contents of one bottle of sterile glucose solution is added to each flask. Culture of A3/5 then proceeds on an Orbital Shaker, with 2 inch throw, at 160 r.p.m. and a temperature of 30° C. The culture is harvested after 18 hours.

Cells were collected and washed on a Buchner filtration system and treated as follows:

(i) Suspended in 66% v/v isopropyl alcohol for 1 minute at 20° C.
(ii) Isopropyl alcohol was removed by filtration.
(iii) The treated cells were incubated in 0.1M $NH_4Cl/NH_4OH$ buffer at pH 8.6 and 45° C. for various times. The incubations were carried out at a slurry concentration of approximately 10 g/l with stirring.

Results

| Microfungi | Treatment | Time of Incubation Minutes | % RNA Content | % Amino Nitrogen | % Total Nitrogen |
|---|---|---|---|---|---|
| F. gramine-arum | None | None | 10.86 | 7.57 | 9.80 |
| | Nucleic acid Reduction | Zero | 9.86 | 8.23 | 10.98 |
| | Nucleic acid Reduction | 20 | 2.29 | 8.84 | 10.45 |
| | Nucleic acid Reduction | 40 | 1.88 | 8.68 | 9.91 |
| | Nucleic acid Reduction | 60 | 1.69 | 8.73 | 10.56 |

Conclusion

The level of nucleic acid was effectively reduced by the treatment described.

*Penicillium notatum chrysogenum* IMI 138291 was cultivated by the following procedure:

Medium

| | |
|---|---|
| 2% | Soluble starch |
| 0.2% | Spray dried corn steep liquor |
| 0.2% | Mycological peptone |
| 0.4% | (NH4)2SO4 |
| 0.2% | KH2PO4 |
| 1% | Sucrose |

The medium is made up with hot tap water, and dispensed in 200 ml. aliquots into conical shake flasks.

0.1 ml. of liquid amylase was added to each shake flask and incubated at 70° C. for 15 minutes so that the starch was broken down and the viscosity reduced.

Sterilisation

The flasks were sterilised in an autoclave at 15 p.s.i. for 20 minutes.

Growth conditions

A spore inoculum was added to each flask and the culture grown at 30° C. on an orbital shaker with a 2 inch throw at 160 r.p.m. After growth for 24 hours, 10 ml. of the growing culture was used as growing inoculum which was added to more flasks containing the starch medium. Cells produced after a further 24 hours growth were harvested, washed and used as follows:

(i) Suspended in 66% (v/v) isopropyl alcohol for one minute at 20° C.
(ii) Isopropyl alcohol was removed by filtration.
(iii) The treated cells were incubated in 0.1M NH4Cl/NH4OH buffer at pH 8.6 and 40° C. for various times. The incubations were carried out at a slurry concentration of approximately 10 gm/l with stirring.

Results

| Microfungi | Treatment | Time of Incubation Minutes | % RNA content | % Amino Nitrogen | % Total Nitrogen | % Biomass Loss |
|---|---|---|---|---|---|---|
| P. notatum-chrysogenum | None | None | 7.19 | 5.78 | 7.58 | 0 |
| P. notatum-chrysogenum | Nucleic Acid Reduction | 15 | 3.60 | 6.64 | 8.47 | 30 |
| P. notatum-chrysogenum | Nucleic Acid Reduction | 40 | 3.25 | 6.47 | 8.52 | 32 |
| P. notatum-chrysogenum | Nucleic Acid Reduction | 60 | 3.32 | 6.34 | 8.04 | 32 |

Conclusion

The level of nucleic acid was reduced by the treatment described.

*Penicillium funiculosum* IMI 79195 was cultivated by the following procedure:

Medium

| | |
|---|---|
| KH2PO4 | 15 g/l |
| NaOH | 1 g/l |
| Dextran | 1 g/l |
| Caster Oil | 10 g/l |
| Solution A+ | 5 ml/l |
| Solution B+ | 5 ml/l |
| Solution C+ | 5 ml/l |
| Yeast extract | 10 g/l |

Minimal salts

| A+ | | B+ | | C+ | |
|---|---|---|---|---|---|
| MgSO4 | 50 g/l | CaCl2 | 3 g/l | FeSO4 | 1 g/l |
| ZnSO4 | 1 g/l | | | | |
| MnSO4 | 1 g/l | CoCl2 | 0.2 g/l | | |
| CuSO4 | 0.2 g/l | | | | |

All in distilled water.

Sterilisation

Adjust pH of medium to 5.5 before sterilisation. Autoclave all components together. (50 minutes 15 p.s.i.)

Growth conditions

| (Batch culture) | Volume 10l. (Fermenter) |
|---|---|
| | Temperature 28° C. |
| | Stirrer 400 r.p.m. |
| | Air flow 10l/minutes |
| | Harvest time 80 hours |
| | Inoculum size 5% by volume (shake flask culture) |

Cells were collected and washed on a Buchner filtration system and treated as follows:

(i) Suspended in 80% isopropyl alcohol for 1 minute at 20° C.
(ii) Isopropyl alcohol was removed by filtration.
(iii) The treated cells were incubated in 0.1M NH4Cl/NH4OH buffer at pH 8.6 and 37° C. for 60 minutes. The incubation was carried out at a slurry concentration of approximately 10 g/l with stirring.

Results

| Micro-organism | Treatment | % RNA content | % Amine N | % Total N |
|---|---|---|---|---|
| P. funiculosum | None | 4.23 | 3.74 | 5.81 |
| P. funiculosum | Nucleic Acid Reduction | 2.80 | 4.46 | 7.34 |

Conclusion

The level of nucleic acid was reduced by the treatment described.

*Aspergillus niger* NRRL 330 was cultivated by the following procedure:

The medium and sterilisation procedure were identical to that described for *P. notatum-chrysogenum*.

Growth conditions were also identical except that cells grown directly from spores were used instead of cells cultivated from growing inoculum.

Cells were collected and washed on a Buchner filtration system and treated as follows:

(i) Suspended in 66% (v/v) isopropyl alcohol for 1 minute at 20° C.

(ii) Isopropyl alcohol was removed by filtration.

(iii) The treated cells were incubated in 0.1M NH₄Cl/NH₄OH buffer at pH 8.6 and 40° C. for various times. The incubations were carried out at a slurry concentration of approximately 10 g/l with stirring.

Results

| Micro-fungi | Treatment | Time of Incubation Minutes | % RNA Content | % Amino Nitrogen | % Total Nitrogen | % Biomass loss |
|---|---|---|---|---|---|---|
| A. niger | None | None | 6.36 | 4.03 | 5.70 | none |
| A. niger | Nucleic acid Reduction | zero | | | | |
| A. niger | Nucleic acid Reduction | 15 | 1.88 | 4.40 | 6.30 | 27 |
| A. niger | Nucleic acid Reduction | 30 | 1.86 | 4.35 | 5.77 | 28 |
| A. niger | Nucleic acid Reduction | 60 | 1.82 | 4.25 | 5.62 | 32 |

Conclusion

The level of nucleic acid was effectively reduced by the treatment described.

EXAMPLE B

Effect of the % Iso-propyl Alcohol on the Efficiency of the Nucleic Acid Reduction Process

*F. graminearum* IMI 145425, cultivated as described in Example A, was contacted with various isopropyl alcohol/water mixtures at 20° C. for 2 minutes. The treated cells were then incubated in 0.1M NH₄Cl/NH₄OH buffer pH 8.5 at 37° C. for 20 minutes. The incubations were carried out at a slurry concentration of approximately 10 g/l with stirring.

Results

| % IPA (by volume) | Treatment | % Biomass loss | % RNA remaining |
|---|---|---|---|
| 0 | None | 0.0 | 9.33 |
| 0 | Nucleic acid reduction | 1.8 | 9.33 |
| 10 | Nucleic acid reduction | 1.1 | 10.68 |
| 20 | Nucleic acid reduction | 11.3 | 9.74 |
| 30 | Nucleic acid reduction | 19.4 | 8.87 |
| 40 | Nucleic acid reduction | 25.6 | 4.58 |
| 50 | Nucleic acid reduction | 26.5 | 3.03 |
| 60 | Nucleic acid reduction | 28.0 | 3.25 |
| 70 | Nucleic acid reduction | 27.6 | 2.86 |
| 80 | Nucleic acid reduction | 26.3 | 3.35 |
| 90 | Nucleic acid reduction | 23.8 | 3.69 |
| 100 | Nucleic acid reduction | 25.1 | 4.58 |

Conclusion

The nucleic acid removal process is most effective in the range of 40–100% isopropyl alcohol.

In the case of the treatment with 10 & 20% IPA the final RNA content is greater than the starting material; this is because RNA is removed to a lesser extent than biomass lost.

EXAMPLE C

Effect of Contact With IPA at Various Temperatures on the Subsequent Nucleic Acid Reduction Process

*F. graminearum* IMI 145425, cultivated as described in Example A, was contacted with 100% IPA at 0°, 20°, 40°, and 60° C. for 2 minutes, then incubated with 0.1M NH₄Cl/NH₄OH buffer pH 8.5 for 20 minutes at 39° C. The incubations were carried out at a slurry concentration of approximately 10 g/l with stirring.

Results

| Temperature of IPA treatment | % RNA remaining |
|---|---|
| No treatment | 9.04 |
| 0° C. | 3.42 |
| 20° C. | 3.47 |
| 40° C. | 2.52 |
| 60° C. | 2.33 |

Conclusion

The nucleic acid reduction process is effective over the temperature range studied.

EXAMPLE D

Effectiveness of Various Alcohols on the Nucleic Acid Reduction Process

*F. graminearum* IMI 145425, cultivated as described in Example A, was contacted with 100% iso-propyl alcohol, 70% iso-propyl alcohol, 70% propyl alcohol, 100% ethyl alcohol or 100% methyl alcohol at 20° C. for two minutes, then incubated with 0.1M $NH_4Cl/NH_4OH$ buffer pH 8.5 at 37° C. or 40° C. for various time periods. The incubations were carried out at a slurry concentration of approximately 10 g/l with stirring.

Results

| Alcohol used | Time and temperature of second incubation | % RNA remaining |
|---|---|---|
| None | None | 9.16 |
| 100% iso-propyl alcohol | 30 mins. at 37° C. | 2.53 |
| 100% iso-propyl alcohol | 120 mins. at 37° C. | 0.70 |
| iso-propyl alcohol | 20 mins. at 40° C. | 1.81 |
| propyl alcohol | 20 mins. at 40° C. | 1.93 |
| 100% ethyl alcohol | 30 mins. at 37° C. | 2.17 |
| 100% ethyl alcohol | 120 mins. at 37° C. | 0.64 |
| 100% methyl alcohol | 30 mins. at 37° C. | 5.50 |
| 100% methyl alcohol | 120 mins. at 37° C. | 1.17 |

Conclusion

The RNA reduction process is successfully activated by a lower alkanol containing up to three carbon atoms.

EXAMPLE E

Duration of Contact With Iso-propyl Alcohol

*F. graminearum* IMI 145425, cultivated as described in Example A, was contacted with 66% (v/v) IPA at 20° C. for various times then incubated in 0.1M $NH_4Cl/NH_4OH$ buffer pH 8.5 at 37° C. for 60 minutes. The incubations were carried out at a slurry concentration of approximately 10 g/l with stirring.

Results

| Contact time with 66% IPA | % RNA remaining | % Biomass lost |
|---|---|---|
| 0 | 9.25 | 0 |
| 15 seconds | 1.12 | 36 |
| 1 minute | 1.14 | 38 |
| 2 minutes | 0.98 | 40 |
| 5 minutes | 1.23 | — |
| 15 minutes | 1.27 | 41 |

Conclusion

Over the contact times studied nucleic acid removal was efficient. In practice the contact time for best RNA reduction is around 2 minutes, at longer contact times the % biomass lost tends to rise to unacceptably high values.

EXAMPLE F

Efficiency of Nucleic Acid Reduction With Buffers Over a pH Range of 4–10

*F. graminearum* IMI 145425, cultivated as described in Example A, was contacted with 100% iso-propyl alcohol at 20° C. and incubated with the following series of buffers at 30° C. for 3 hours. The incubations were carried out at a slurry concentration of approximately 10 g/l with stirring.

Results

| Buffer in second stage | % RNA Remaining |
|---|---|
| 0.1 M $NH_4Cl$ + HCl to bring to pH 4.0 | 11.49 |
| 0.1 M $NH_4Cl$ + HCl to bring to pH 4.5 | 9.07 |
| 0.1 M $NH_4Cl$ + HCl to bring to pH 5.0 | 5.85 |
| 0.1 M $NH_4Cl$ + HCl to bring to pH 5.5 | 3.52 |
| 0.1 M $NH_4$ + $NH_4OH$ to bring to pH 6.0 | 2.63 |
| 0.1 M $NH_4$ + $NH_4OH$ to bring to pH 6.5 | 1.60 |
| 0.1 M $NH_4$ + $NH_4OH$ to bring to pH 7.0 | 0.96 |
| 0.1 M $NH_4$ + $NH_4OH$ to bring to pH 7.5 | 0.97 |
| 0.1 M $NH_4$ + $NH_4OH$ to bring to pH 8.0 | 0.59 |
| 0.1 M $NH_4$ + $NH_4OH$ to bring to pH 8.5 | 0.91 |
| 0.1 M $NH_4$ + $NH_4OH$ to bring to pH 9.0 | 1.69 |
| 0.1 M $NH_4$ + $NH_4OH$ to bring to pH 9.5 | 3.84 |
| 0.1 M $NH_4$ + $NH_4OH$ to bring to pH 10.0 | 7.00 |

Conclusion

The nucleic acid removal is effective with this buffer system over the pH range 5–9.5.

EXAMPLE G

Efficiency of Nucleic Acid Reduction Carried Out in Buffers of Varying Ionic Strengths

*F. graminearum* IMI 145425 cultivated as described in Example A, was contacted with 66% (v/v) IPA at 20° C. for 1 minute, and incubated in buffers or non-buffered solutions of varying ionic strengths at 45° C. The incubations were carried out at approximately 10 g/l with stirring.

Results

| Buffer system | Treatment | Time of incubation at 45° C. (Minutes) | % RNA | % Amino Nitrogen | % Total Nitrogen |
|---|---|---|---|---|---|
| None | None | None | 10.89 | 7.57 | 9.80 |
| Distilled | Nucleic acid reduced | 0 | 11.21 | 7.82 | 10.53 |
| water | " | 20 | 7.38 | 8.07 | 10.22 |
| pH 5.7 | " | 40 | 4.79 | 7.97 | 10.12 |
| | " | 60 | 2.57 | 8.40 | 9.84 |
| Non-buffered | " | 0 | 11.17 | 8.35 | 10.81 |

-continued

| Buffer system | Treatment | Time of incubation at 45° C. (Minutes) | % RNA | % Amino Nitrogen | % Total Nitrogen |
|---|---|---|---|---|---|
| ammonia solution sufficient to bring to pH 8.5 | " | 20 | 4.54 | 8.85 | 10.07 |
| | " | 40 | 3.14 | 8.85 | 10.68 |
| | " | 60 | 2.55 | 8.79 | 10.30 |
| 0.02M NH₄Cl/NH₄OH buffer pH 8.5 | " | 0 | 9.96 | 8.46 | 10.89 |
| | " | 20 | 3.21 | 8.62 | 10.38 |
| | " | 40 | 2.39 | 8.73 | 10.36 |
| | " | 60 | 1.82 | 8.90 | 10.12 |
| 0.1M NH₄Cl/NH₄OH buffer pH 8.5 | " | 0 | 9.86 | 8.23 | 10.98 |
| | " | 20 | 2.29 | 8.84 | 10.45 |
| | " | 40 | 1.88 | 8.68 | 9.91 |
| | " | 60 | 1.69 | 8.73 | 10.56 |
| 0.5M NH₄Cl/NH₄OH buffer pH 8.5 | " | 0 | 10.02 | 8.21 | 10.58 |
| | " | 20 | 5.85 | 8.35 | 10.13 |
| | " | 40 | 5.63 | 8.42 | 10.01 |
| | " | 60 | 5.58 | 8.54 | 10.12 |
| 1.0M NH₄Cl/NH₄OH buffer pH 8.5 | " | 0 | 10.19 | 7.56 | 10.89 |
| | " | 20 | 10.45 | 7.72 | 10.48 |
| | " | 40 | 9.96 | 7.99 | 10.81 |
| | " | 60 | 9.89 | 8.15 | 10.58 |

Conclusion

Nucleic acid is most effectively reduced at lower ionic strengths. The optimum conditions for rapid reduction being 0.1M buffer.

EXAMPLE H

The Nucleic Acid Reduction Process Studied at Various Temperatures

*F. graminearum* IMI 145425, cultivated as described in Example A, was contacted with 66% (v/v) IPA at 20° C. for 2 minutes, and incubated in 0.1M NH₄Cl/NH₄OH buffer pH 8.5 for various durations at various temperatures. The incubations were carried out at approximately 10 g/l with stirring.

Results

| Temperature of buffer | Time of incubation minutes | % RNA remaining |
|---|---|---|
| Control | — | 9.44 |
| 30° C. | 0 | 10.83 |
| 30° C. | 20 | 8.40 |
| 30° C. | 40 | 7.06 |
| 30° C. | 60 | 7.45 |
| 30° C. | 90 | 4.76 |
| 30° C. | 120 | 4.11 |
| 37° C. | 0 | 10.12 |
| 37° C. | 20 | 5.02 |
| 37° C. | 40 | 3.55 |
| 37° C. | 60 | 3.55 |
| 37° C. | 90 | 1.80 |
| 37° C. | 120 | 1.02 |
| 45° C. | 0 | 10.09 |
| 45° C. | 20 | 2.58 |
| 45° C. | 40 | 0.99 |
| 45° C. | 60 | 0.69 |
| 45° C. | 90 | 0.69 |
| 45° C. | 120 | 0.61 |
| 55° C. | 1.5 | 2.16 |
| 55° C. | 3.0 | 1.10 |
| 55° C. | 4.5 | 0.76 |
| 60° C. | 1.5 | 1.96 |
| 60° C. | 3.0 | 1.78 |
| 60° C. | 4.5 | 1.11 |
| 70° C. | 2.0 | 4.19 |
| 70° C. | 3.5 | 3.30 |
| 70° C. | 5.0 | 3.56 |
| 80° C. | 1.5 | 5.65 |
| 80° C. | 3.0 | 5.40 |
| 80° C. | 4.5 | 5.31 |

Conclusion

Nucleic acid reduction takes place over the temperature range 30° C.–80° C. The most efficient conditions are at a temperature of 60° C., where satisfactory reduction of RNA was achieved within 90 seconds.

According to the present invention there is provided a process for reducing the nucleic acid content in the production of an edible protein-containing substance which comprises maintaining a grown non-toxic microfungus of the class Fungi Imperfecti in a suspension at a pH between 4.7 and 7.0 and at a temperature between 55° and 72° C. for a time of at least 60 seconds.

The process may be applied to a grown non-toxic strain of Fusarium.

The strain of Fusarium may be a strain of *Fusarium graminearum* Schwabe in particular IMI 145425, *Fusarium oxysporum* or *Fusarium solani* as described and claimed in our Applications Nos. 23452/70 (Ser. No. 1,346,061) and 30584/70 and cognate 10466/71 (Ser. No. 1,346,062).

The grown non-toxic microfungus of the class Fungi Imperfecti may conveniently be maintained in a suspension at a pH between 4.7 and 7.0 and at a temperature between 55° and 68° C. for a time of at least 200 seconds.

The post fermentation process of the present invention for reducing the nucleic acid content of microorganisms is essentially a single-stage process.

The grown microbial protein or fungal mycelium obtained for example by the fermentation process described and claimed in our Application No. 30584/70 and cognate No. 10466/71 (Ser. No. 1,346,062), may be harvested, filtered to remove growth medium and washed, if desired. The cells may then be brought into intimate contact with aqueous buffer solutions in the pH range 4.7 to 7.0. Thus the cells may then be resuspended and incubated in tap water at pH 6.3 and temperature 63° C. for a period of 20 minutes.

The resulting treated cells may then be harvested again for example by filtration and washing with water and thereafter formulated into foods or dried by various methods.

In order to confine the loss of protein to a minimum it is desirable to raise the temperature of the cell suspension to a given temperature within the range of 55° and 72° C. as rapidly as possible; substantially the same temperature may subsequently be maintained for a period of 5 to 60 minutes.

An optional prior step designed to inhibit or destroy the proteolytic activity comprises maintaining a grown non-toxic microfungus of the class Fungi Imperfecti at the selected isothermal temperature of between 55° and 72° C. at a pH where there is no proteolytic activity for a time sufficient to destroy the protease but not the ribonuclease.

Thus with a view to improving the protein economy of the present isothermal process the cells may be held at a pH of 8.5 at the selected isothermal temperature, preferably 65° C., for a duration of between ½ minute and 5 minutes, preferably 1 minute before the isothermal process is commmenced (i.e. with an adjustment of the pH to between 4.7 and 7).

The resulting fungal mycelium may have an RNA content of 1 to 4% compared to 7 to 12% of the untreated proliferated organism. In certain instances the RNA content may be less than 1%.

The cells may be analysed to determine their chemical composition and to evaluate the efficiency of the nucleic acid reduction process.

Following is a description of methods of determining the chemical composition.

References to "Biomass Loss" denote weight loss during processing.

Ribonucleic acid (RNA) content is determined by a modification of the method of Schneider, W. C. Analyst, 1945, 161, 293.

Method of analysis for Total Nitrogen (TN) Automatic Kjeldahl digester (Technicon), A. Ferrari, Ann. N.Y. Sci 87, 792.

Amino nitrogen (AN) TNBS (modified). M. A. Pinnegar, Technicon Symposium 1965, p. 80.

Following is a description by way of example of methods of carrying the invention into effect.

*Fusarium graminearum* IMI 145425 was cultivated continuously by the following procedure:

| Medium in tap water: | |
|---|---|
| Potato Starch (treated with α-amylase and glucamylase) | 60 g/l |
| MgSO$_4$ 7H$_2$O | 0.75 g/l |
| ZnSO$_4$ 7H$_2$O | 10.0 mg/l |
| CuSO$_4$ 5H$_2$O | 2.0 mg/l |
| NaMoO$_4$ 2H$_2$O | 2.0 mg/l |
| CoCl 6H$_2$O | 2.0 mg/l |
| MnSO$_4$ 4H$_2$O | 10.0 mg/l |
| FeSO$_4$ 7H$_2$O | 20.0 mg/l |
| NH$_4$H$_2$PO$_4$ | 3.0 g/l |
| K$_2$SO$_4$ | 2.4 g/l |
| NaCl | 0.125 g/l |
| Boric acid | 0.5 mg/l |
| Biotin | 0.005 mg/l |
| PPG 2000 | 0.04 mg/l |
| Fermenter operation conditions | |
| Temperature | 30° C. |
| pH | 6.0 |
| Pressure | 15.5 psig |
| Stirrer speed | 230 rpm |
| Air flow | 800 l/minute |
| Dissolved oxygen | 6.5 (arbitary units where air saturation is 80) |
| Sterilisation Temperature | 135° C. by continuous sterilisation (90 secs holding time) |
| Dilution rate | 0.14 hr$^{-1}$ |
| Fermenter Volume | 1300 l |
| Inoculum: Prior to continuous growth the fermenter was operated in a batch fashion from a 20 l inoculum of a growing culture. When batch growth was complete the fermenter was put on stream under the above conditions. | |

Note

In some of the examples which follow the % RNA content is not corrected for "Biomass Loss".

e.g. 100 g cells $\xrightarrow{\text{RNA Reduction process}}$ 70 g treated cells + 30 g Biomass Loss (Containing say 10 g RNA)   (Containing say 2 g RNA)

The % RNA content not corrected for Biomass Loss is 2% (ie 2 g from the original 100 g of cells Whereas the % RNA corrected for Biomass Loss is $\frac{2}{70}$ × 100 = 2.86% (ie 2 g in a final 70 g of product)

The Isothermal Process like other RNA reduction processes generally results in approximately 30% Biomass loss. However because the biomass loss is not generally determined on each sample it becomes necessary to quote RNA content of the product as a function of the starting material.

Results

EXAMPLE A

The Nucleic Acid Reduction Process Studied at Various Temperatures

*F. graminearum* IMI 145425, cultivated as described earlier was harvested and washed on a Buchner filtration system. The cells were suspended at a slurry concentration of approximately 10 g/l in tap water at various temperatures for various durations.

Results

| Treatment | Temperature of Incubation °C. | Duration of Incubation minutes | % RNA Content (Not corrected for Biomass Loss) | % of the original RNA remaining |
|---|---|---|---|---|
| Control | 55 | — | 8.09 | 100 |
| Nucleic Acid reduction | 55 | 5 | 8.09 | 100 |
| Nucleic Acid reduction | 55 | 10 | 6.58 | 81 |
| Nucleic Acid reduction | 55 | 20 | 3.40 | 42 |
| Nucleic Acid reduction | 55 | 40 | 1.16 | 14 |
| Nucleic Acid reduction | 55 | 60 | 0.80 | 10 |
| Control | 58 | — | 7.56 | 100 |
| Nucleic Acid reduction | 58 | 5 | 6.26 | 83 |
| Nucleic Acid reduction | 58 | 10 | 3.55 | 47 |
| Nucleic Acid reduction | 58 | 20 | 1.79 | 24 |
| Nucleic Acid reduction | 58 | 30 | 1.21 | 16 |
| Nucleic Acid reduction | 58 | 45 | 0.88 | 12 |
| Control | 60 | — | 10.84 | 100 |
| Nucleic Acid reduction | 60 | 5 | 8.15 | 75 |

| Treatment | Temperature of Incubation °C. | Duration of Incubation minutes | % RNA Content (Not corrected for Biomass Loss) | % of the original RNA remaining |
|---|---|---|---|---|
| Nucleic Acid reduction | 60 | 10 | 4.92 | 45 |
| Nucleic Acid reduction | 60 | 20 | 2.39 | 22 |
| Nucleic Acid reduction | 60 | 30 | 1.68 | 15 |
| Nucleic Acid reduction | 60 | 45 | 1.29 | 12 |
| Control | 62 | — | 9.85 | 100 |
| Nucleic Acid Reduction | 62 | 1 | 11.25 | — |
| Nucleic Acid Reduction | 62 | 5 | 6.37 | 65 |
| Nucleic Acid Reduction | 62 | 10 | 4.19 | 43 |
| Nucleic Acid Reduction | 62 | 20 | 2.30 | 23 |
| Nucleic Acid Reduction | 62 | 30 | 1.83 | 19 |
| Control | 64 | — | 11.34 | 100 |
| Nucleic Acid Reduction | 64 | 1 | 11.96 | — |
| Nucleic Acid Reduction | 64 | 5 | 6.12 | 54 |
| Nucleic Acid Reduction | 64 | 10 | 4.10 | 36 |
| Nucleic Acid Reduction | 64 | 20 | 2.70 | 24 |
| Nucleic Acid Reduction | 64 | 30 | 2.39 | 21 |
| Control | 66 | — | 8.22 | 100 |
| Nucleic Acid Reduction | 66 | 1 | 7.03 | 86 |
| Nucleic Acid Reduction | 66 | 5 | 3.13 | 38 |
| Nucleic Acid Reduction | 66 | 10 | 2.29 | 28 |
| Nucleic Acid Reduction | 66 | 20 | 1.99 | 24 |
| Nucleic Acid Reduction | 66 | 30 | 2.18 | 27 |
| Control | 68 | — | 8.47 | 100 |
| Nucleic Acid Reduction | 68 | 1 | 6.78 | 80 |
| Nucleic Acid Reduction | 68 | 5 | 3.03 | 36 |
| Nucleic Acid Reduction | 68 | 10 | 2.56 | 30 |
| Nucleic Acid Reduction | 68 | 20 | 2.44 | 29 |
| Nucleic Acid Reduction | 68 | 30 | 2.36 | 28 |
| Control | 70 | — | 7.51 | 100 |
| Nucleic Acid Reduction | 70 | 1 | 3.29 | 44 |
| Nucleic Acid Reduction | 70 | 5 | 2.65 | 35 |
| Nucleic Acid Reduction | 70 | 10 | 2.40 | 32 |
| Nucleic Acid Reduction | 70 | 20 | 2.33 | 31 |
| Nucleic Acid Reduction | 70 | 30 | 2.22 | 30 |
| Control | 72 | — | 7.62 | 100 |
| Nucleic Acid Reduction | 72 | 1 | 5.35 | 70 |
| Nucleic Acid Reduction | 72 | 5 | 2.74 | 36 |
| Nucleic Acid Reduction | 72 | 10 | 2.43 | 32 |
| Nucleic Acid Reduction | 72 | 20 | 2.33 | 31 |
| Nucleic Acid Reduction | 72 | 30 | 2.33 | 31 |
| Control | 75 | — | 9.16 | 100 |
| Nucleic Acid Reduction | 75 | 1 | 6.02 | 66 |
| Nucleic Acid Reduction | 75 | 5 | 5.10 | 57 |
| Nucleic Acid Reduction | 75 | 10 | 5.04 | 55 |
| Nucleic Acid Reduction | 75 | 20 | 4.73 | 52 |
| Nucleic Acid Reduction | 75 | 30 | 4.49 | 49 |
| Control | 80 | — | 8.72 | 100 |
| Nucleic Acid Reduction | 80 | 1 | 5.69 | 65 |
| Nucleic Acid Reduction | 80 | 5 | 5.26 | 60 |
| Nucleic Acid Reduction | 80 | 10 | 5.11 | 59 |
| Nucleic Acid Reduction | 80 | 20 | 4.57 | 52 |
| Nucleic Acid Reduction | 80 | 30 | 4.51 | 52 |

Conclusions

With mould cultivated in the manner described it is possible to reduce the nucleic acid level to acceptably low values within the temperature range 55°–72° C.

The ideal isothermal temperature depends on the extent of RNA removal desired and the duration which can be tolerated on economic grounds.

The preferred conditions for our purposes are pH 6, 62.5° C. for 18 minutes (see also Example B).

EXAMPLE B

Efficiency of Nucleic Acid Reduction Over a pH Range of 4–9.5 at 62.5

F. graminearum IMI 145425, cultivated as described earlier was harvested and washed on a Buchner filtration system. The cells were suspended in tap water at 62.5° C. and a slurry concentration of approximately 10 g/l. The pH was controlled at the desired value by automatic addition of either HCl or NH$_4$OH. Samples were incubated for 18 minutes.

Results

| Treatment | pH of incubation | Duration of incubation minutes | % of RNA in product | % AN | % TN | % Biomass Loss | % of the original RNA remaining | % of the original AN remaining in the product |
|---|---|---|---|---|---|---|---|---|
| Control | — | — | 8.24 | 5.9 | 7.68 | — | 100 | 100 |
| Isothermal at 62.5° C. | 9.5 | 18 | 7.31 | 6.27 | 8.60 | 23.9 | 67.5 | 81 |
| Isothermal at 62.5° C. | 9.0 | 18 | 8.36 | 6.36 | 8.77 | 21.4 | 79.7 | 84.7 |

-continued

| Treatment | pH of incubation | Duration of incubation minutes | % of RNA in product | % AN | % TN | % Bio mass Loss | % of the original RNA remaining | % of the original AN remaining in the product |
|---|---|---|---|---|---|---|---|---|
| Isothermal at 62.5° C. | 8.5 | 18 | 8.29 | 6.31 | 8.52 | 20.8 | 79.7 | 84.7 |
| Isothermal at 62.5° C. | 8.0 | 18 | 8.28 | 6.19 | 8.41 | 21.4 | 79.0 | 82.5 |
| Isothermal at 62.5° C. | 7.0 | 18 | 2.06 | 6.34 | 7.74 | 28.3 | 17.9 | 77.0 |
| Isothermal at 62.5° C. | 6.0 | 18 | 1.01 | 6.46 | 7.80 | 31.4 | 8.4 | 75.1 |
| Isothermal at 62.5° C. | 5.0 | 18 | 1.39 | 6.48 | 7.95 | 32.1 | 11.4 | 74.6 |
| Isothermal at 62.5° C. | 4.0 | 18 | 7.26 | 6.48 | 8.49 | 27.7 | 63.7 | 79.4 |

Conclusions (1) The pH optimum for the process carried out at 62.5° C. is in the range pH 4.7–7.0. Maximum reduction was at pH 6.0.
(2) Unfortunately, optimum pH for protein retention is not pH 6.0 but pH 8.5–9.0.
(3) Observations on colours: The dried solids, moist filter cakes and slurries at pH's of 6.0 and above were dark grey. Those at pH 5.0 were fawn, and at pH 4.0 the material was white. After the RNA reduction has been accomplished it may therefore be desirable to adjust the pH to 4.0 to obtain a white product.

EXAMPLE C

Efficiency of Nucleic Acid Reduction Carried Out in Solutions of Varying Logic Ionic Strengths

*F. graminearum* IMI 145425, cultivated as described earlier was harvested and washed on a Buchner filtration system. The cells were suspended at a slurry concentration of approximately 10 g/l in solutions of varying ionic strengths. The pH was automatically maintained at pH 6 and the incubation was carried out at 62.5° C. for a duration of 20 minutes.

Results

| Treatment | Incubation Solution (maintained at pH 6) | % RNA in product | % Amino Nitrogen | % Total Nitrogen |
|---|---|---|---|---|
| Control | — | 8.58 | 6.63 | 8.85 |
| Nucleic Acid Reduction | Distilled water | 1.50 | 7.12 | 8.69 |
| Nucleic Acid Reduction | 0.01 M NaCl | 1.18 | 6.98 | 8.81 |
| Nucleic Acid Reduction | 0.05 M NaCl | 1.05 | 6.99 | 9.04 |
| Nucleic Acid Reduction | 0.10 M NaCl | 1.04 | 7.06 | 8.96 |
| Nucleic Acid Reduction | 0.20 M NaCl | 0.87 | 6.69 | 8.64 |
| Nucleic Acid Reduction | 0.50 M NaCl | 0.91 | 6.77 | 8.50 |
| Nucleic Acid Reduction | 0.50 M NH$_4$Cl | 0.62 | 7.02 | 8.64 |

Conclusions

In the range studied NaCl and NH$_4$Cl had little effect on the nucleic acid reduction process.

EXAMPLE D

Efficiency of Nucleic Acid Reduction at Various Slurry Concentrations

*F. graminearum* IMI 145425, cultivated as described earlier was harvested and washed on a Buchner filtration system. The cells were suspended at various slurry concentrations in tap water at 63° C. for various durations.

Results

|

-continued

| Treatment | Slurry Concentration g/l | Time of Incubation (minutes-seconds) | % RNA Content (Not corrected for biomass loss) |
|---|---|---|---|
| Reduction |  |  |  |
| Nucleic Acid Reduction | 40 g/liter | 5.10 | 5.25 |
| Nucleic Acid Reduction | 40 g/liter | 15.00 | 1.68 |
| Nucleic Acid Reduction | 40 g/liter | 30.50 | 1.02 |

Conclusion

The results show that broadly speaking slurry concentration only affects RNA reduction in as much as heat transfer is affected (i.e. high slurry concentrations may require stirring to ensure rapid temperature equilibration).

EXAMPLE E

Efficiency of Nucleic Acid Reduction Under Various Agitation Conditions

F. graminearum IMI 145425, cultivated as described earlier was harvested and washed on a Buchner filtration system. The cells were suspended at approximately 10 g/liter in tap water at 63° C. under various agitation conditions.

Results

| Treatment | Agitation in Grant Water Bath strokes/minute | Duration of incubation minutes | % RNA Content (Not corrected for Biomass Loss) |
|---|---|---|---|
| None (Control) | None | None | 8.30 |
| Nucleic Acid Reduction | Zero | 1 | 7.31 |
| Nucleic Acid Reduction | Zero | 5 | 2.33 |
| Nucleic Acid Reduction | Zero | 10 | 1.04 |
| Nucleic Acid Reduction | Zero | 20 | 0.67 |
| Nucleic Acid Reduction | Zero | 30 | 0.59 |
| Nucleic Acid Reduction | 50 | 1 | 7.44 |
| Nucleic Acid Reduction | 50 | 5 | 2.59 |
| Nucleic Acid Reduction | 50 | 10 | 1.23 |
| Nucleic Acid Reduction | 50 | 20 | 0.84 |
| Nucleic Acid Reduction | 50 | 30 | 0.74 |
| Nucleic Acid Reduction | 250 | 1 | 6.26 |
| Nucleic Acid Reduction | 250 | 5 | 2.10 |
| Nucleic Acid Reduction | 250 | 10 | 1.37 |
| Nucleic Acid Reduction | 250 | 20 | 1.13 |
| Nucleic Acid Reduction | 250 | 30 | 1.13 |

Conclusion

The results show that it is not necessary to stir the slurry during the Isothermal process. The effect of shaking at this slurry concentration is negligible. This has tremendous implications from the chemical engineering point of view when scale-up to larger plant is carried out.

EXAMPLE F

Typical Nucleic Acid Reduction Experiment

F. graminearum IMI 145425, cultivated as described earlier was harvested and washed on a Buchner filtration system. The cells were resuspended at a slurry concentration of approximately 10 g/l in a solution of 0.1M NaCl. The pH was automatically maintained at pH 6 and the incubation was carried out at 62.5 C. for a duration of 20 minutes.

Results

| 100 g of fungus containing | | 68.1 g product | 31.9 g Biomass Lost |
|---|---|---|---|
| 37.30 g protein | | 30.00 g protein + | |
| 4.70 g amino acids | isothermal process → | — | |
| 8.58 g RNA | | 0.71 g RNA | |

Conclusion

The product contains 44% protein and 0.8% ribonucleic acid i.e. a protein to nucleic acid ratio of 55:1. The starting material contains 37.3% protein and 8.58% ribonucleic acid i.e. a protein to nucleic acid ratio of 4.35:1.

EXAMPLE G

An Optional Prior Process Designed to Destroy the Protease Activity Without Substantially Destroying the Ribonuclease Activity

*F. graminearum* IMI 145425, cultivated as described earlier was harvested and washed on a Buchner filtration system. The cells were suspended in distilled water at 65° C. and a slurry concentration of approximately 10 g/l. The pH was controlled at 8.5 for various times.

After this prior treatment the cells were subjected to RNA removal by the isothermal process at 65° C., pH 6 for 20 minutes.

Results

| Treatment | % of RNA in product | % AN in product | % TN in product | % Biomass Loss |
|---|---|---|---|---|
| Control | 8.37 | 6.26 | 8.31 | Zero |
| ½ minutes at pH 8.5 + 20 min pH 6 | 1.09 | 7.03 | 9.12 | 43.4 |
| 1 minute at pH 8.5 + 20 min pH 6 | 1.31 | 7.23 | 9.49 | 35.0 |
| 2 minutes at pH 8.5 + 20 min pH 6 | 1.52 | 7.21 | 9.38 | 35.4 |
| 5 minutes at pH 8.5 + 20 min pH 6 | 2.52 | 7.24 | 9.38 | 31.4 |

Conclusions

The optimal example which removes the maximum quantity of RNA but at the same time retains maximal Biomass and amino nitrogen is fulfilled by conditions of 1 minutes at 65° C. and pH 8.5 followed by the isothermal process at 65° C. pH 8.5 for 20 minutes.

Examples of Successful Reduction of the Nucleic Acid Levels in Various Micro-organisms Other Than A3/5

EXAMPLE H

*Fusarium solani* IMI 154217 was cultivated by the following procedure:

Medium in distilled water:

| | |
|---|---|
| $MgSO_4.7H_2O$ | 0.25 g/liter |
| $KH_2PO_4$ | 15.0 g/liter |
| $(NH_4)_2SO_4$ | 2.83 g/liter |
| Biotin | 0.05 ml/liter (of stock solution 1 mg/ml) |
| Choline | 50 mg/liter |
| Trace elements | 5 ml/liter (STOCK SOLUTION) |
| NaOH | 1 g/liter→ pH 6.0 |
| Glucose | 10% solution (20 mls added after sterilization) |

Minimal Salts or Trace element stock solution

| | |
|---|---|
| $ZnCl_2$ | 1 g/liter |
| $MnCl_24H_2O$ | 1 g/liter |
| $FeCl_36H_2O$ | 2 g/liter |
| $CuCl_22H_2O$ | 0.2 g/liter |
| $NaMnO_42H_2O$ | 0.2 g/liter |
| $CoCl_26H_2O$ | 0.2 g/liter |
| $CaCl_22H_2O$ | 2 g/liter |

Sterilisation

All components with the exception of glucose were sterilised together, and the quantity of these materials required for 1 liter of medium were dissolved, made up to 850 ml and distributed in 5 1 liter conical flasks, each containing 170 ml. A 0.10% w/v solution of glucose was prepared and sterilized in 20 ml portions in universal bottles. Sterilisation was effected in an autoclave at 15 p.s.i. for 15 minutes.

Growth Conditions

Before inoculation with 10 ml of a spore suspension, the contents of one bottle of sterile glucose solution were added to each flask. Culture of the organism then proceeded on an Orbital Shaker, with 2 inch throw, at 160 r.p.m and a temperature of 30° C. The culture was harvested after 48 hours.

Nucleic Acid Reduction Process

Cells were collected and washed on a Buchner filtration system and suspended at a slurry concentration of approximately 10 g/liter in tap water at 64° C. and the pH adjusted to 6 with NaOH and $H_2SO_4$.

Results

| Microfungi | Treatment | Time of incubation | % RNA content | % amino nitrogen |
|---|---|---|---|---|
| F. solani | None | None | 5.15 | 5.4 |
| | Nucleic Acid Reduction | 10 | 2.95 | 5.92 |
| | Nucleic Acid Reduction | 20 | 0.67 | 6.11 |
| | Nucleic Acid Reduction | 30 | 0.55 | 6.00 |

Conclusion

The level of Nucleic acid was effectively reduced by the treatment described.

EXAMPLE I

*Fusarium oxysporum* IMI 154214 was cultivated in a similar manner to that described for *F. solani* except that the growth medium contained 0.5 g/liter oxoid yeast extract and 0.5 g/liter mycological peptone in addition to the chemicals listed in Example H.

The cells were harvested after 72 hours and the nucleic acid reduction process conducted as in the previous example.

Results

| Microfungi | Treatment | Time of incubation minutes | % RNA content | % amino nitrogen |
|---|---|---|---|---|
| F. oxysporum | None | None | 6.57 | 6.28 |
| | Nucleic Acid Reduction | 10 | 1.00 | 7.47 |
| | Nucleic Acid Reduction | 20 | 0.65 | 7.45 |
| | Nucleic Acid Reduction | 30 | 0.54 | 7.53 |

Conclusion

The level of Nucleic acid was effectively reduced by the treatment described.

EXAMPLE J

The Nucleic Acid Reduction Process as Carried Out in Pilot Plant

*F. graminearum* IMI 145425, cultivated as described earlier was processed without separation from the growth medium as follows:

1. Mycelium slurry at a concentration of 20 grams per liter exists from the fermenter at a temperature of 30° C. and a pH of 6 and enters a mono-pump.
2. The mycelial slurry is pumped to a steam injector and the temperature of the material raised from 30° C. to 64° C. rapidly, the duration of the temperature rise, preferably being instantaneous (in practice being less than 5 seconds).
3. The material now at 64° C. and pH 6 is moved through a pipe and its temperature maintained for a duration of 45 minutes.
4. The material is passed through a heat exchanger to cool to approximately 20° C. (to reduce the possibility of later microbial infection).
5. The slurry is passed into the trough of a rotary vacuum filter.
6. Liquid is drawn through a filter belt and the mycelium accumulates on the filter. The filter drum rotates above the liquid level carrying the mycelial cake.
7. The filter cake is washed with about 2 bed volumes of water. The filter drum continues to rotate and a vacuum pulls the cake to about 70% moisture by weight.
8. The mycelial cake is scraped off the drum.
9. The cake is reslurried in water and spray dried.

Results

| Treatment | % RNA Content | % Amino Nitrogen Content | % Total Nitrogen Content |
|---|---|---|---|
| Dry untreated | 8.22 | 6.45 | 8.74 |

-continued

| Treatment | % RNA Content | % Amino Nitrogen Content | % Total Nitrogen Content |
| --- | --- | --- | --- |
| material | | | |
| Dry nucleic acid reduced material | 0.43 | 6.86 | 8.30 |

Conclusion

The nucleic acid content is effectively reduced by the process described.

In the fermentation operation conditions it is possible to employ a higher dilution rate of up to 0.20 hrs$^{-1}$, for example 0.17 hrs$^{-1}$.

We claim:

1. An edible protein-containing substance comprising a non-viable edible non-toxic fungal mycelium of a non-toxic strain of Fusarium possessing a reduced level of RNA of below 2%, and being further characterized by improved ease of processing to a form suitable for food use and an essentially white color such to make the protein-containing substance compatible with food use and a filamentous structure.

2. An edible protein-containing substance comprising a non-viable edible non-toxic fungal mycelium of a non-toxic strain of Fusarium selected from the group consiting of *Fusarium graminearum, Fusarium solani,* and *Fusarium oxysporum* possessing a reduced level of RNA of below 1.5%, and being further characterized by improved ease of processing to a form suitable for food use and an essentially white color such to make the protein-containing substance compatible with food use and a filamentous structure.

3. An edible protein-containing substance comprising a non-viable edible non-toxic fungal mycelium of a non-toxic strain of *Fusarium graminearum* Schwabe deposited with the Commonwealth Mycological Institute and assigned the number IMI 145425 (A.T.C.C. No. 20334) possessing a reduced level of RNA of below 1.29%, and being further characterized by improved ease of processing to a form suitable for food use and an essentially white color such to make the protein-containing substance compatible with food use and a filamentous structure.

4. An edible protein-containing substance comprising a non-viable edible non-toxic fungal mycelium of a non-toxic strain of Fusarium, said product having a filamentous structure and possessing a reduced level of RNA of between approximately 0.8% and approximately 0.43%, and being further characterized by improved ease of processing to a form suitable for food use and an essentially white color such to make the protein-containing substance compatible with food use.

5. An edible protein-containing substance in the form of a cohesive sheet comprising a non-viable edible non-toxic fungal mycelium of a non-toxic strain of Fusarium, said product having a high net protein utilization value of the order of 41 or above based on total nitrogen and possessing a reduced level of RNA of between approximately 0.67% and approximately 0.43%, and being further characterized by improved ease of processing to a form suitable for food use and an essentially white color such to make the protein-containing substance compatible with food use and a filamentous structure.

6. An edible protein-containing substance comprising a non-viable edible non-toxic fungal mycelium of a non-toxic strain of *Fusarium graminearum* Schwabe I.M.I. 145425 (A.T.C.C. No. 20334), said product having a high net protein utilization value of the order of 52 or above based on total nitrogen and possessing a reduced level of RNA of approximately 0.43%, and being further characterized by a white color such to make the protein-containing substance compatible with food use and a filamentous structure, and being capable of processing by vacuum filtration in the form of a washed moist product suitable for food use.

* * * * *

UNITED STATES PATENT AND TRADEMARK OFFICE
CERTIFICATE OF CORRECTION

PATENT NO. : 4,466,988                    Page 1 of 2
DATED      : August 21, 1984
INVENTOR(S): Peter J. TOWERSEY, et al.

It is certified that error appears in the above-identified patent and that said Letters Patent is hereby corrected as shown below:

In the left column of the heading, in the second line of "[*] Notice", for "Mar. 9, 1994" read -- Aug. 9, 1994 --.

Column 5, line 14, "Methionic" should be -- Methionine --.

Column 6, line 39, "NaMoO$_4$2H$_2$O" should be --Na$_2$MoO$_4$2H$_2$O --.

Column 7, line 52, "FeSO$_4$:(NH$_2$)$_2$SO$_4$:6H$_2$O" should be

-- FeSO$_4$:(NH$_4$)$_2$SO$_4$:6H$_2$O --.

Column 10, line 22 "(who)" should be -- (WHO) --.

Column 17, line 35, "iso-propyl alcohol" should be

-- 70% iso-propyl alcohol --.

UNITED STATES PATENT AND TRADEMARK OFFICE
CERTIFICATE OF CORRECTION

PATENT NO. : 4,466,988

DATED : August 21, 1984

INVENTOR(S) : Peter J. TOWERSEY, et al.

It is certified that error appears in the above-identified patent and that said Letters Patent is hereby corrected as shown below:

Column 17, line 36, "propyl alcohol" should be

-- 70% propyl alcohol --.

Column 25, Example C, line 2, "Logic" should be deleted.

Column 30 line 38, "exists" should be -- exits --.

Signed and Sealed this

Twelfth Day of March 1985

[SEAL]

Attest:

DONALD J. QUIGG

Attesting Officer

Acting Commissioner of Patents and Trademarks

UNITED STATES PATENT AND TRADEMARK OFFICE
CERTIFICATE OF CORRECTION

PATENT NO. : 4,466,988
DATED : August 21, 1984
INVENTOR(S) : TOWERSEY et al.

It is certified that error appears in the above-identified patent and that said Letters Patent is hereby corrected as shown below:

Title page:

In the second line of "[30] Foreign Application Priority Date", for "Oct. 8, 1975" read --Feb. 13, 1973 --, and for "7087/75" read --7087/73--.

Signed and Sealed this

Twentieth Day of May 1986

[SEAL]

Attest:

Attesting Officer

DONALD J. QUIGG

Commissioner of Patents and Trademarks